United States Patent
LeJeune et al.

(10) Patent No.: US 7,422,892 B2
(45) Date of Patent: Sep. 9, 2008

(54) ENZYME-BASED DEVICE FOR ENVIRONMENTAL MONITORING

(75) Inventors: Keith E. LeJeune, Pittsburgh, PA (US); Richard J. Mysliwczyk, Pittsburgh, PA (US); Paul L. Holzapfel, Mercer, PA (US); Markus Erbeldinger, Pittsburgh, PA (US)

(73) Assignee: Agentase, LLC, Pittsburgh, PA (US)

( * ) Notice: Subject to any disclaimer, the term of this patent is extended or adjusted under 35 U.S.C. 154(b) by 537 days.

(21) Appl. No.: 10/959,744

(22) Filed: Oct. 6, 2004

(65) Prior Publication Data

US 2006/0073490 A1   Apr. 6, 2006

(51) Int. Cl.
*C12M 1/34* (2006.01)

(52) U.S. Cl. .......................... 435/288.7; 435/6; 435/20; 435/23

(58) Field of Classification Search ...................... 435/6, 435/20, 23, 288.7
See application file for complete search history.

(56) References Cited

U.S. PATENT DOCUMENTS

| | | | |
|---|---|---|---|
| 3,715,298 A * | 2/1973 | Goodson et al. | 204/403.14 |
| 4,066,412 A | 1/1978 | Johnson et al. | |
| 4,224,033 A | 9/1980 | Hansen et al. | |
| 4,324,858 A | 4/1982 | Goodson et al. | |
| 4,338,280 A | 7/1982 | Ambers et al. | |
| 4,525,704 A | 6/1985 | Campbell et al. | |
| 4,726,929 A | 2/1988 | Gropper et al. | |
| 4,826,759 A | 5/1989 | Guire et al. | |
| 4,958,295 A | 9/1990 | Davidson et al. | |
| 5,223,224 A | 6/1993 | Dremel et al. | |
| 5,504,006 A | 4/1996 | Rindt et al. | |
| 5,858,186 A | 1/1999 | Glass | |
| 5,935,572 A * | 8/1999 | Hayward et al. | 424/94.2 |
| 5,945,343 A | 8/1999 | Munkholm | |
| 5,958,786 A | 9/1999 | Munkholm | |
| 5,994,091 A | 11/1999 | Attridge et al. | |
| 6,291,200 B1 * | 9/2001 | LeJeune et al. | 435/20 |
| 6,514,689 B2 * | 2/2003 | Han et al. | 435/4 |
| 6,673,565 B2 | 1/2004 | LeJeune et al. | |
| 6,750,033 B2 | 6/2004 | LeJeune et al. | |
| 6,759,220 B1 | 7/2004 | LeJeune et al. | |

(Continued)

OTHER PUBLICATIONS

Rogers, K.R., Biosensors for Environmental Applications, Biosensors and Bioelectronics, 1995, 533-541, vol. 10, Issues 6-7, Elsevier Science Ltd.

(Continued)

*Primary Examiner*—Walter D. Griffin
*Assistant Examiner*—Shanta G Doe
(74) *Attorney, Agent, or Firm*—Buchanan Ingersoll & Rooney PC; Craig G. Cochenour

(57) ABSTRACT

A sensor for the intermittent or continuous detection of the presence of at least one analyte in an environmental sample includes at least one enzyme that is selected to either (i) catalyze a reaction of the analyte to chemically convert the analyte to a product compound or (ii) be inhibited by the analyte in the presence of a substrate compound. The sensor also includes at least one sensor for monitoring or at least one indicator compound selected to produce a measurable change of state as a result of the interaction of the analyte and the enzyme. Optionally, each of the enzyme and the indicator compound are incorporated within a single polymer.

25 Claims, 4 Drawing Sheets

Schematic of continuous sensor.

U.S. PATENT DOCUMENTS

2001/0056328 A1* 12/2001 Trippel et al. ............... 702/19
2002/0182662 A1* 12/2002 Lejeune et al. ............... 435/18

OTHER PUBLICATIONS

Parente A.H. et al., Glucose Biosensor Using Glucose Oxidase Immobilized in Polyaniline, Appl. Biochemistry and Biotechnology, 1992, 267-273, vol. 37, The Humana Press Inc., Totowa, NJ.

Yang, S. et al., Glucose Biosensors Based on Oxygen Electrode with Sandwich-Type Membranes, Annals of Biomedical Engineering, 1995, 833-839, vol. 23, Biomedical Engineering Society, Landover, MD.

* cited by examiner

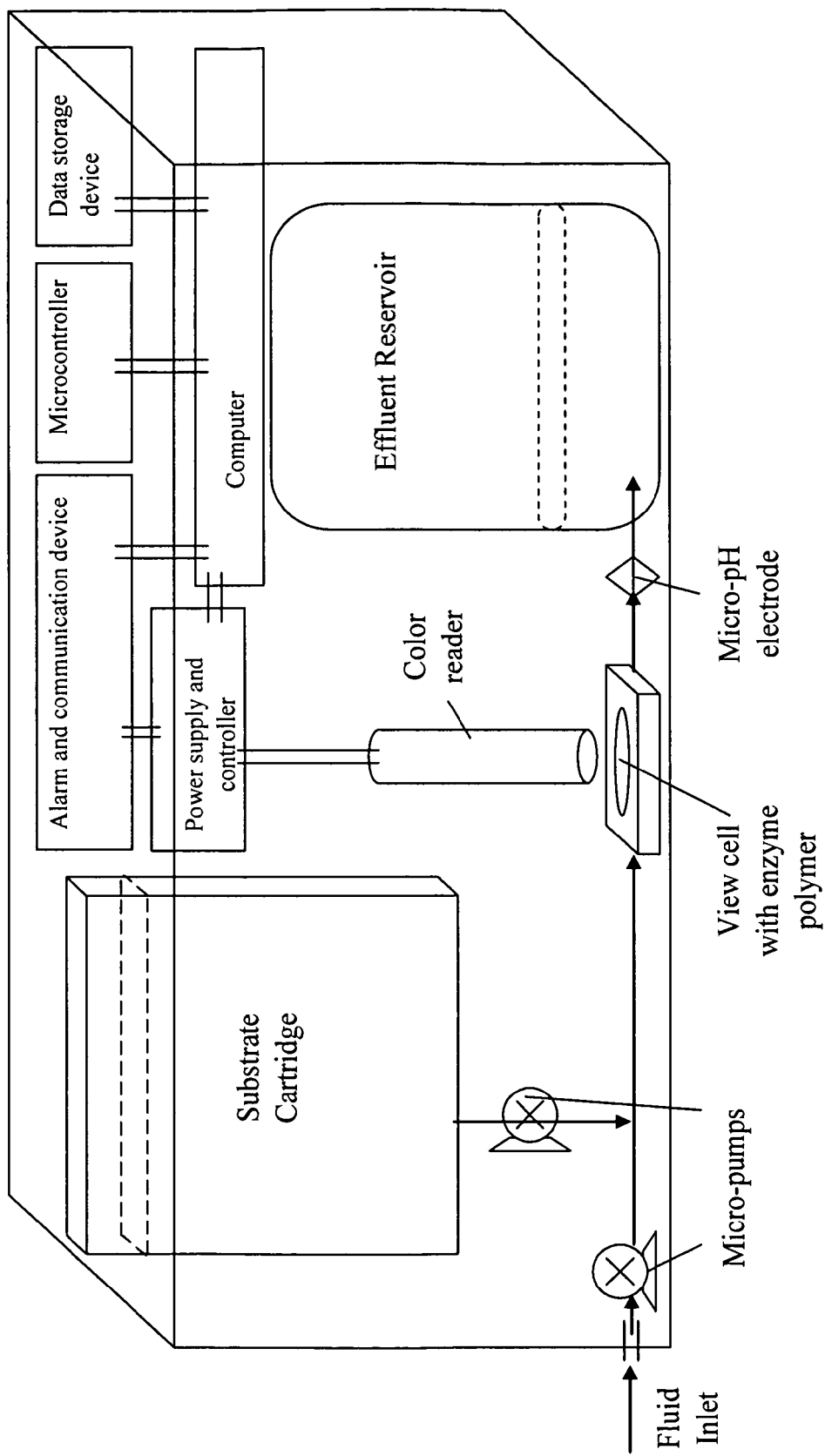
Figure 1. Schematic of continuous sensor.

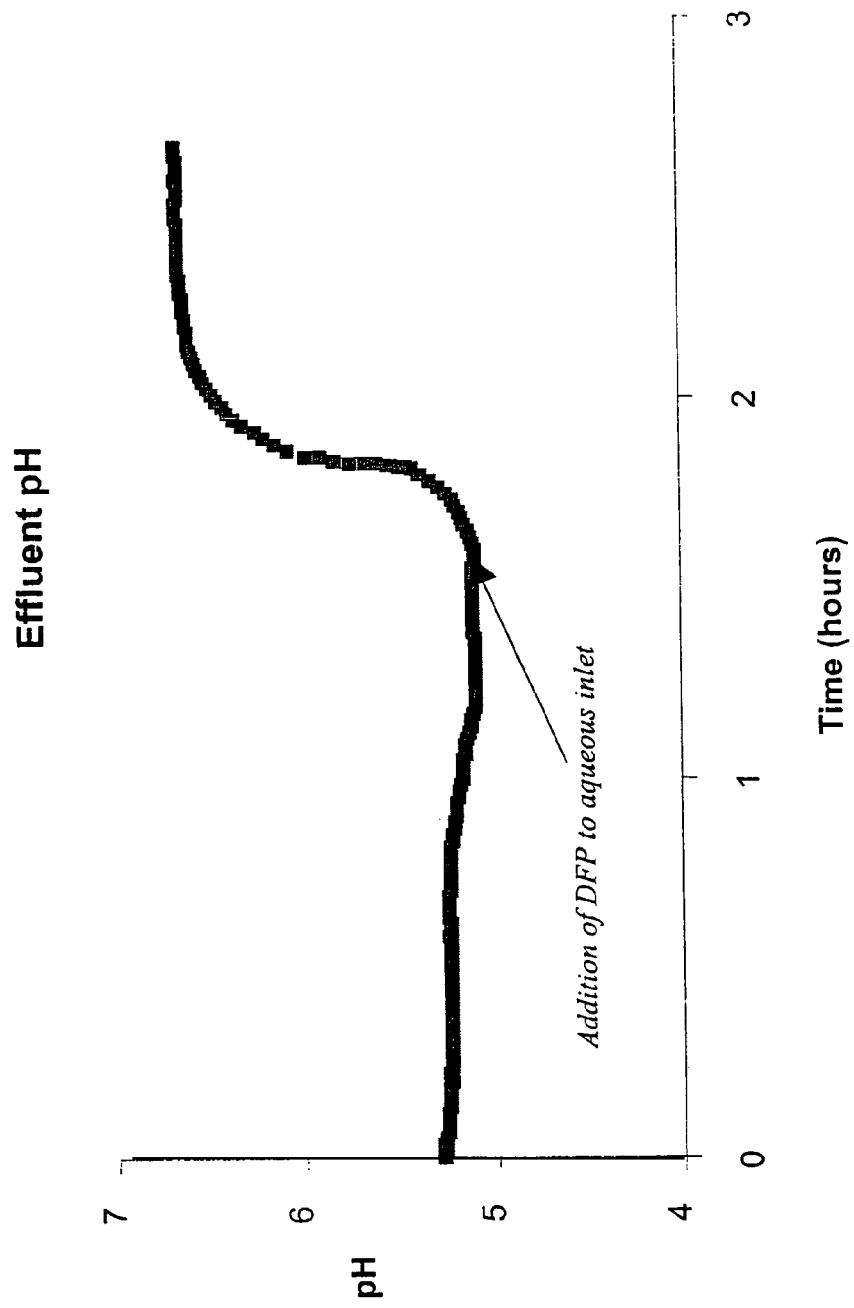
Figure 2. Effluent response to presence of cholinesterase inhibitors in sample.

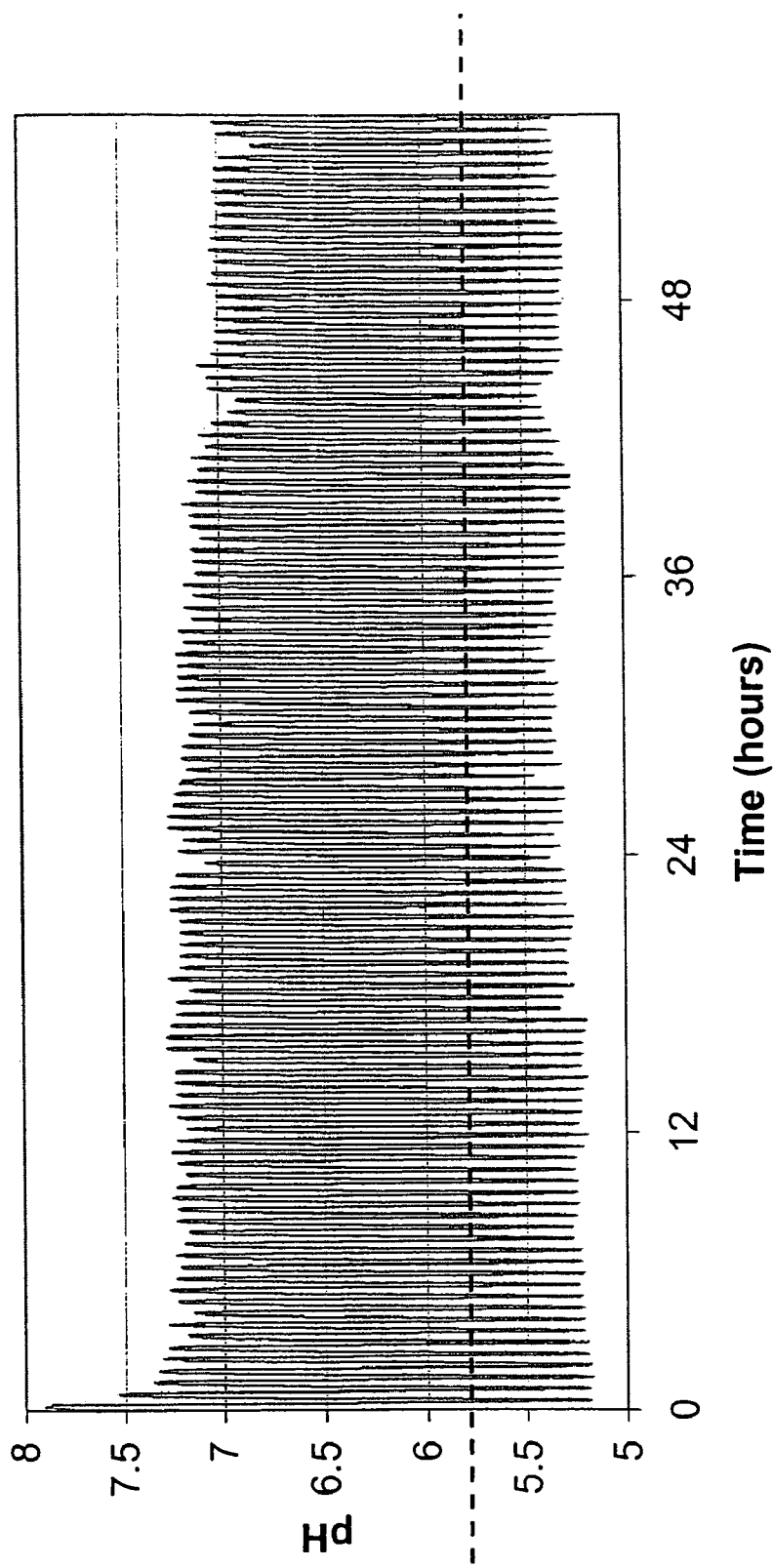
Figure 3. The sensor is stable for extended periods of operation.

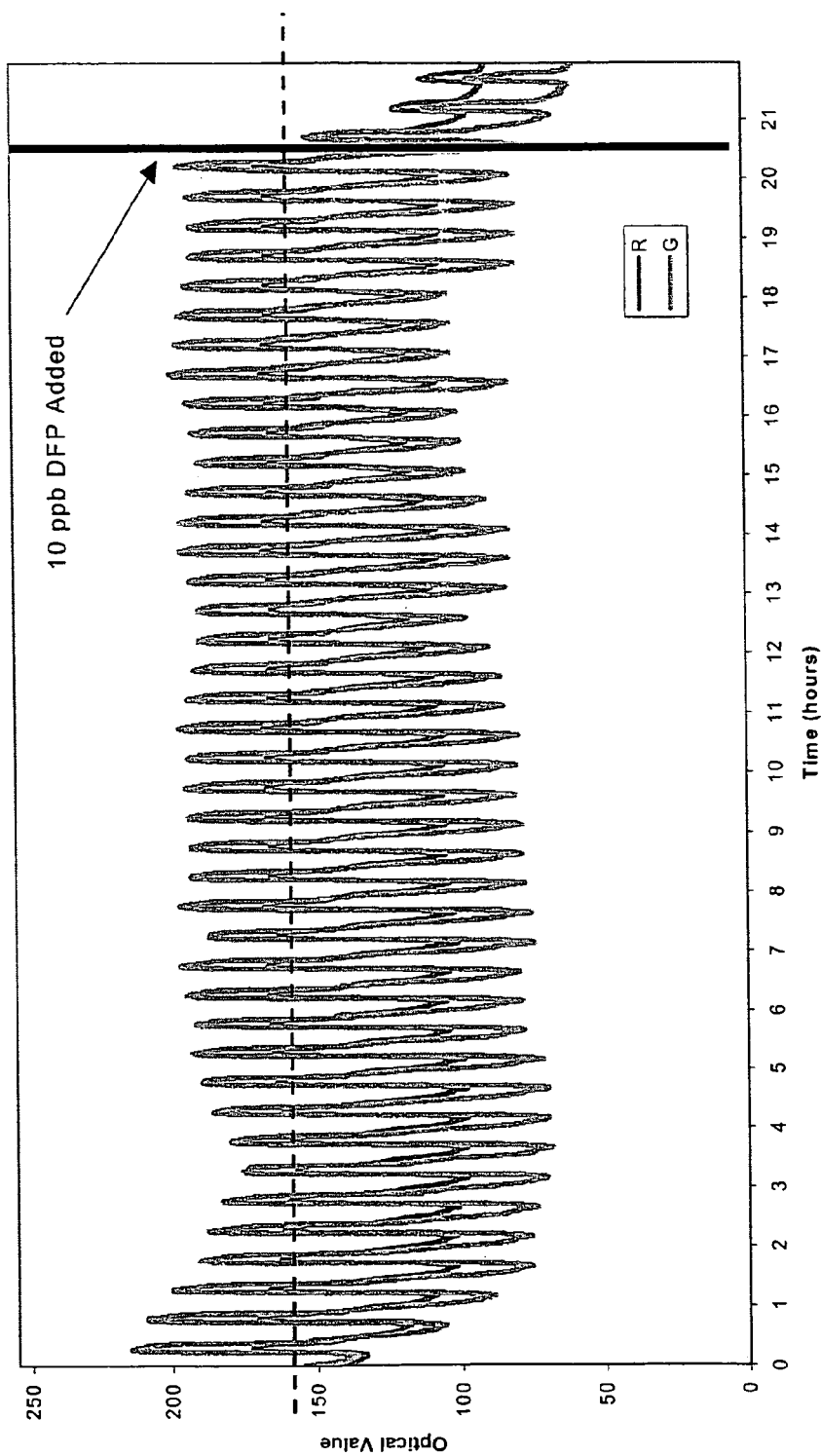
Figure 4. Color response can be used to detect enzyme inhibitors

ENZYME-BASED DEVICE FOR ENVIRONMENTAL MONITORING

GOVERNMENT INTEREST

Certain embodiments of this invention was made with Government support under Contract No. DMI0319086 awarded by the National Science Foundation. The Government has certain rights in the invention.

FIELD OF THE INVENTION

The present invention relates to a device that employs an enzyme-based sensor to continuously monitor the environment for the presence of target chemicals and, especially, to a device that employs an enzyme or enzymes to detect the presence of an enzyme inhibitor within the environment without the active involvement of a user.

BACKGROUND OF THE INVENTION

Enzymatic proteins are remarkable natural catalysts that selectively catalyze many reactions under relatively mild reaction conditions. Enzymes also offer the potential to perform sterio- and regio-selective reactions not readily accomplished with conventional chemistry. As used herein, the term "enzyme" refers generally to proteins that catalyze biochemical reactions. These "biopolymers" include amide-linked amino acids and typically have molecular weights of 5,000 or greater. A compound for which a particular enzyme catalyzes a reaction is typically referred to as a "substrate" of the enzyme.

In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases.

Enzymes have been known since the early 1960's to be useful tools for detecting the presence of chemical species. Rogers, K. R., *Biosensors Bioelectronics*, 10, 533 (1995). Generally all enzymatic biosensors function by one of two methods. The enzyme either converts an undetectable compound of interest into another or series of compounds which can be detected with a chemical-based sensor or the enzyme is inhibited by the presence of the compound of interest and the enzyme inhibition is linked to a measurable quantity.

Enzymatic biosensors have been designed to detect a variety of different compounds such as glucose, creatinine, urea, and cholinesterase inhibitors. Parente, A. H., Marques, E. T. Jr., *Appl. Biochem. Biotechnol.* 37, 3, 267 (1992); Yang, S., Atanasov, P., Wilkins, E., *Ann. Biomed. Eng.*, 23, 6, 833 (1995). U.S. Pat. No. 5,858,186 describes a urea-based biosensor in which substrate hydrolysis is monitored with a pH electrode. U.S. Pat. Nos. 5,945,343 and 5,958,786 describe enzyme-based sensors in which a fluorophere is immobilized in a first polymer layer and an enzyme is separately immobilized in a second polymer layer. The fluorophere layer fluoresces in the presence of ammonia, which is enzymatically produced from urea and creatinine (respectively, with respect to U.S. Pat. Nos. 5,945,343 and 5,958,786). In addition, U.S. Pat. No. 4,324,858 describes the immobilization of cholinesterase within a porous, dry material for the colormetric detection of organophosphorus pesticides and nerve agents.

It is very desirable to develop a device that employs enzyme-based sensors in a continuous manner for monitoring the environment for the presence of target analytes such as pollutants, target industrial chemicals, or other hazardous chemicals. The development of monitoring devices for sampling and for chemical identification and detection has also been previously put to practice.

Much of the art related to device development focuses on equipment for use in laboratories as automated samplers or fluid handling equipment. U.S. Pat. Nos. 4,224,033 and 4,338,280 each describe fluid handling devices that facilitate the hands-free processing of individual liquid samples in a preparatory fashion for later analysis and evaluation. Similarly, U.S. Pat. No. 4,066,412 discloses a device that can carry disposable reagents to aid in monitoring the physical properties of a reaction mixture by passing light through a fixed solution path length.

Other relevant art describes devices that employ specialized components to facilitate the use of particular sensing chemistries and protocols for fluid analysis. U.S. Pat. No. 4,826,759 describes a fluid sampling device that carries two adsorbent layers that are used to bring fluid components into the device and transfer such elements to a second layer for chemical analysis. Others, U.S. Pat. Nos. 4,726,929 and 4,958,295, describe modular devices that handle and analyze fluids in unique ways including disposable sample collection modules and internal vacuum drives, respectively.

The present invention describes an enzyme-based device for the continuous monitoring of gases or liquids for the presence of target enzyme inhibitors. The use of enzymes within analytical devices is not, in itself, novel. U.S. Pat. No. 4,525,704 describes the use of cholinesterases and electrical currents in detecting toxic gases. Other patents describe devices that can be used to detect the presence of enzyme substrates within a specified sample. U.S. Pat. No. 5,223,224 describes an arrangement for flow injection analysis in which sample gases are kept isolated from the environment within the device. U.S. Pat. Nos. 5,504,006 and 5,994,091 both describe sensor devices to sample gas and liquid streams, respectively, for enzyme substrates by linking enzyme activity brought on by the presence of such substrate to a colorimetric signal.

SUMMARY OF THE INVENTION

The present invention provides a device that employs an enzyme and substrate pair to continuously monitor an incoming sample for the presence of an enzyme inhibitor. The sensor includes at least one immobilized enzyme that is selected to be inhibited by the analyte. The device also includes a mechanism to continuously, or semi-continuously, deliver a substrate compound to the immobilized enzyme. The same, or a second, delivery mechanism is respectively employed to bring an environment sample (air or water) into coordinated intermittent or simultaneously continuous contact with the immobilized enzyme. A final component of the device detects the level of enzyme activity on the delivered substrate and compares such activity level to an established baseline. Significant reduction in enzyme activity is indicative of the presence of the target analyte (an enzyme inhibitor) within the environment.

There are a number of specific operational and hardware requirements for a viable monitoring device. Enzyme activity within the immobilization matrix must be maintained during operation. This necessitates that the immobilized enzymes not leach from the immobilization matrix during the normal course of operation within the device. The enzyme must also have sufficient thermal stability to maintain high levels of catalytic activity under normal operating conditions and temperatures.

The enzyme substrates or reactants that are to be delivered to the immobilized enzyme during operation must also meet certain basic criteria. Substrates must be capable of being packaged in a manner that they are stable for extended periods of time without special storage conditions in order for the operation of an enzyme-based continuous monitoring device to be practicable. Substrates must also be stable within the device for extended periods under operational conditions.

The fluid delivery mechanisms for substrate (liquid) and sample (liquid or gas) to the immobilized enzyme and detection mechanism must be precise, maintainable, and well coordinated. Major deviations in flow rates or timing between coordinated flow changes in excess of 20% may be problematic for the unit, resulting in erroneous data output from the detection mechanisms.

Detection mechanisms within the device may employ one of many technologies but ideally should utilize a combination of technologies to reduce the risk of false (positive or negative) detection events. By requiring that multiple detection mechanisms indicate the presence of target chemicals prior to triggering an alarm, false positive responses that are a product of shortcomings of individual detection technologies are negated.

To facilitate these requirements the enzyme is preferably chemically bonded to the immobilization matrix, but can also be physically entrapped as long as the entrapment process is efficient. More preferably, the enzyme is covalently bonded to a polymer matrix as described in LeJeune and Russell, U.S. Pat. No. 6,759,220, the text of which is incorporated by reference herein. The use of covalently-linked enzyme polymers as disposable single-use sensors has been described in U.S. Pat. Nos. 6,291,200, 6,750,033, and 6,673,565, the text of each of which is incorporated by reference herein.

In one embodiment, the enzyme is a hydrolase enzyme and detection methodologies employ pH electrodes and dye compounds that change color as a function of reactor effluent pH. Examples of suitable hyrolase enzymes include, but are not limited to, a lipase, a phosphatase, an amylase, a cellulase, a protease, a peptidase, a urease or a deaminase. Specific examples of suitable hydrolases include, but are not limited to, organophosphorus hydrolase, organophosphorus acid anhydrolase, urease, butyrylcholinesterase or acetylcholinesterase. One or a plurality of types of enzymes can be incorporated within the polymer to detect one or a plurality of analytes. Examples of pH-sensitive dyes suitable for use with such enzymes include, but are not limited to, Brilliant green, crystal violet, methyl green, picric acid, Eosin Y, thymol blue, xylonel blue, Eosin B, cresol red, methyl yellow, ethyl orange, bromocresol green, Alizarin Red, bromomethyl blue, bromocresol purple, phenol red, and chlorophenol red.

In another aspect, the present invention provides a method for detecting the presence of at least one analyte. The method includes the step of sampling the environment via either water or air intake. As described above, the device includes hardware components that move the sample through the device to an immobilized enzyme preparation. The enzyme preparation is exposed to the flowing sample and simultaneously or intermittently exposed to an enzyme-reactant solution. The levels of enzyme activity, which are monitored by a downstream detector, are indicative of the presence of any enzyme inhibitor within the environmental sample. Sufficient quantities of inhibitor within the environmental sample result in reduced levels of enzyme activity in the presence of the substrate solution.

BRIEF DESCRIPTION OF THE DRAWINGS

FIG. 1 is a schematic of the invention.
FIG. 2 illustrates the pH of the device effluent under one operational scenario.
FIG. 3 illustrates the data output form the in-line effluent pH electrode during a particular operational scenario.
FIG. 4 illustrates the data output from the color reader within the device under a period of extended operation.

DETAILED DESCRIPTION OF THE INVENTION

In the present invention, different hydrolase enzymes were incorporated into polyurethane polymers during polymer synthesis. The process of polymerizing enzymes as such is described in LeJeune and Russell, U.S. Pat. No. 6,759,220, incorporated by reference herein.

Resulting enzyme-polyurethanes were utilized as immobilized enzymes within the present invention. They are well suited to such an application due to their permanent chemical links to incorporated enzymes. Their high porosity and flow-through characteristics as well as excellent thermal stability are also attractive for continuous monitoring applications.

EXPERIMENTAL PROCEDURES

1. Enzyme and Dye-Containing Polymer Synthesis

As known in the art, variations of the reaction conditions during synthesis of polyurethanes affect both the physical properties of the resultant foam as well as the degree of enzyme-foam interaction. Described below is a typical procedure for biopolymer synthesis. Initially, 4 ml of pH 7.8 Tris buffer (10 mM) containing Pluronic F-68 surfactant (0.8 to 1 wt %) were placed into a narrow cylindrical mixing vessel. Subsequently, an enzyme solution (for example, 1 ml of 1.5 mg/ml urease in the same buffer) was added. Finally, approximately 4 ml of Hypol™ prepolymer, available from The Dow Chemical Company, (preheated to 30° C. to limit handling problems due to high viscosity) were added to the mixture. The solutions were then intimately mixed. During the initial "cream" period, the solution was injected into a cylindrical mold where it rose and then set within 2 to 5 minutes. Polymer synthesis was complete in less than 10 minutes. The $CO_2$ evolved during the reaction of water and isocyanate lifted the foam to a final volume of approximately 50 to 60 ml. After the initial 10 minute "set-up" time, foam samples were removed from their mold and processed to forms that fit within the monitoring device.

The mixing system used in the studies of the present invention required 30 to 40 seconds of mixing at 2500 rpm to create a high quality foam with Hypo 3000, a toluene di-isocyanate based prepolymer. The mixing system included an oar-shaped metal loop having a height of 3.2 cm and a diameter of 1.3 cm. Hypol 5000 (methylene bis(p-phenyl isocyanate) based), a more hydrophobic prepolymer, required additional mixing. Insufficient mixing leaves un-reacted residual prepolymer dispersed within a dense hard mass of polyurethane. Overmixing does not allow the evolving $CO_2$ to act in lifting the foam. Properly mixed foam will generally increase approximately 6 fold in volume throughout the course of the reaction.

In general, an aqueous solution of enzymes were contacted with an isocyanate-based prepolymer under sufficient agitation to initiate reaction. The enzyme may, for example, be added as a freeze-dried powder or aqueous solution that is either pure or impure. The term "impure" a used herein refers to enzymes containing, for example, other proteins/enzymes and biological molecules. Virtually any protein, enzyme or combination of proteins and/or enzymes can be co-immobilized within the same polymer.

In model studies of the present invention, polymers both with and without enzyme(s) were synthesized. Enzymes studied included urea aminohydrolase, butyrylcholinesterase, papain, trypsin, and acetylcholinesterase. The efficacy of using enzyme-containing polymers in sensing applications within the present invention was demonstrated with a series of substrate solutions and inhibitor solutions/vapors. The details of these experiments and procedures employed therein are described below.

2. Continuous Monitor for Cholinesterase Inhibitors in Water

The device shown in FIG. 1 was used to monitor a water sample for the presence of cholinesterase inhibitors. Water was continuously sampled from a point source by withdrawing a constant flow (10 ml/hr) with a simple pump. A second pump was used to deliver substrate and pH-sensitive dye (200 mM butyrylcholine, 0.8 mg/ml bromocresol purple, 50 mM phosphate buffer at pH 7) from the substrate reservoir into the flow of sampled water. The combined water and substrate streams were delivered to a butyryl cholinesterase carrying (1 mg per gram polymer) polyurethane polymer, which was synthesized as described earlier. The enzyme activity within the polymer decreases pH of the substrate solution from pH 7 (purple color) to below pH 5.5 (yellow color) as the solution flows through the polymer. The effluent color and pH is maintained as long as the sample is free of cholinesterase inhibitors. As can be seen in FIG. 2, the system responds to a cholinesterase inhibitor in the sample stream (10 ppm di-isopropyl fluorophosphates [DFP, FIG. 2]) by incurring an increase of pH and a corresponding color change from yellow to purple within the effluent. The observed response is due to the inhibition of cholinesterase activity within the enzyme polymer.

3. Improved Continuous Monitoring for Cholinesterase Inhibitors in Water

Identical hardware and the same enzyme polymer, as set forth herein, were employed under different operating conditions for improved detection capability. This scenario operates by first flowing the water stream with unknown contents through the enzyme-based polyurethane polymer. Any exposure time (from about 1 to about 30 minutes demonstrated with the device of the present invention) is compatible with operation. An alternating switch simultaneously stops water flow (50 mL/h) and initiates flow of the enzyme-substrate solution (15 mL/h-25 mM butyrylcholine chloride, 5 mM phosphate buffer pH 7 and 0.08 mg/ml bromocresol purple dye) from the reservoir through the same polymer. The purple substrate solution becomes yellow upon exposure to the polymer, due to the polymer's cholinesterase activity. Color change is again accompanied by a fixed pH change (~7 to <5.5), which is straightforwardly monitored with the in-line pH electrode. The color change of the solution is monitored with a simple RGB (red, green, blue) color to frequency converter and micro-controller system (commercially avaibable from TAOSinc, Texas Advanced Optoelectronic Solutions, Plano, Tex.). Outputs from the pH electrode and color monitor are recorded. Data can be stored onboard the device, directly outputted, or wirelessly outputted. The inlet switch repeatedly alternates the water and substrate flows at fixed intervals to provide continuous monitoring capability. Because this device format exposes the enzyme polymer to sampled water in the absence of substrate, sensitivity is greatly increased.

FIG. 3 shows data output for a period of 60 hours of continuous operation of the device. An untreated spring water sample was monitored for the presence of cholinesterase inhibitors under the operational conditions described above. The data output from the effluent pH electrode showed a consistent pattern over the entire period of sensor operation. The zig-zag curve is typical for the alternating substrate/water sample flow system. During the substrate flow portion of the cycle, the polymer hydrolyzes incoming substrate to produce acid and a corresponding pH decrease. When the water-sampling portion of the cycle begins, the water stream washes the reaction products from the polymer and the effluent takes on the pH of the inlet water stream. The water sample is deemed clean as long as the pH falls below about 5.6 during the substrate flow phase of operation within this embodiment. Positive detection is defined as any point at which the pH of the effluent of substrate flow cycle is above about 5.6.

The RBG (red, blue, green) reader can interpret color of the flowing solution or read directly from the polymer. Output is sent to a micro-controller, which can assess if the color represents a clean or contaminated source. The calorimetric RGB reader shows a similar pattern to that of the pH electrode. The reader returns values for red, green, and blue, however only the values for red (see FIG. 4 legend "R") and green (see FIG. 4 legend "G") are shown in FIG. 4, as they are better indicators of a purple to yellow color transition. During the substrate flow cycle, the reactor effluent is yellow due to enzyme activity. The following water-sampling phase increases effluent pH while rinsing residual pH indictor from the polymer (causing the effluent to be purple). It is important to note that the peaks of the data curve in FIG. 4 coincide with the valleys of that in FIG. 3. A positive detection event is therefore defined as one in which the green (G) color value does not exceed about 160 optical value on the 0-255 scale of color development during the substrate flow cycle. FIG. 4 shows the systems response to 10-ppb cholinesterase inhibitor. Note that this cholinesterase inhibitor concentration is far less than that described in example 2. Improved detection is due to sampling inhibitor in the absence of high concentrations of enzyme substrates.

4. Continuous Monitoring for Cholinesterase Inhibitors in Air

A chamber was constructed into which the sensor device of this invention was placed. Air within the chamber was forced over/through the enzyme-polymer using a small fan. The chamber includes an injection port to insert the hazard using a gas-tight syringe with a valve. In initial experiments a substrate stream (25 mM butyrylcholine chloride, 5 mM phosphate buffer pH 7 and a pH sensitive dye (0.08 mg/ml bromocresol purple)) was fed to a 60 mg enzyme polymer (1 mg butyryl cholinesterase per gram polymer) at a flowrate of 1 mL per hour. Upon contact with the polymer, the immobilized enzyme hydrolyzes butyrylcholine to choline and butyric acid. The acid production drives pH downward, and causes a subsequent color change in the polymer and flowing substrate solution from purple to yellow (below pH 5). The polymer remains yellow as long as substrate is supplied and sufficient activity resides in the polymer. If the environment becomes contaminated with a nerve agent (cholinesterase inhibitor) such as di-isopropyl fluorophosphate (DFP) vapor at any time during operation, enzyme activity is reduced and the polymer turns purple. In one particular experiment, the system was running for 3 hours before the air within the chamber was contaminated with 0.5 mg/m3 di-isopropyl fluorophosphate vapor. In this case the polymer rapidly transitioned from yellow to purple within a few minutes of exposure. This same system has been operated for about four days while retaining enzyme activity in the absence of inhibitors.

5. Continuous Monitoring for Iodoacetamide in Water

The device shown in FIG. 1 was used to monitor a water sample for the presence of iodoacetamide. Water was continuously sampled from a point source by withdrawing a constant flow (10 ml/hr) with a simple pump. A second pump was used to deliver a papain substrate solution and pH-sensitive dye (25 mM N-Benzoyl-L-arginine ethyl ester, 0.8 mg/ml bromocresol purple, 60 mg/ml NaCl, 2.8 mg/ml EDTA, 3.3 mg/ml L-cysteine, and 5 mM phosphate buffer at pH 7) from the substrate reservoir into the flow of sampled water. The combined water and substrate streams were delivered to a papain carrying (100 units per gram polymer) polyurethane polymer, which was synthesized as described earlier. The enzyme activity within the polymer decreases pH of the substrate solution from pH 7 (purple color) to below pH 4.9 (yellow color) as the solution flows through the polymer. The effluent color and pH is maintained as long as the sample is free of papain inhibitors. The system responded to iodoacetamide (papain inhibitor) in the sample stream (10 ppm di-isopropyl fluorophosphate) by incurring an increase of pH to near 7.0 and a corresponding color change from yellow to purple within the effluent. The observed response is due to the inhibition of papain activity within the enzyme polymer.

6. Continuous Monitoring for Cholinesterase Inhibitors in Air Using the Dynamic Equilibrium Approach The device described in example 3 was used to monitor the presence of cholinesterase inhibitors in air using the dynamic equilibrium approach as described in LeJeune and Erbeldinger, U.S. Pat. No. 6,750,033 and incorporated by reference herein, using two enzymes, one for the target chemical and the other to shift the pH. Specifically, a substrate stream containing substrates for butyryl cholinesterase and urease (100 mM butyrylcholine chloride, 50 mM urea) and a pH sensitive dye (0.01 mg/mL cresol red)) was fed to a 100 mg polymer (6 mg butyryl cholinesterase, 1.75 mg urease and 1 mg cresol red pH dye per gram polymer) at a flowrate of 1 mL per hour. The system operated in a clean environment for 16 hours while maintaining the pH equilibrium of ~7.4 (and the accompanying yellow color). Upon exposure to 20 ppb di-isopropyl fluorophosphate vapor within the same environment, the equilibrium was disrupted and the pH rapidly fell, causing the polymer to turn red. Either the change in pH or color can be used to identify the presence of contamination.

7. Continuous Monitoring for Paraoxon in Water Using Catalytic Reaction to Convert the Analyte to a Product Compound The device shown in FIG. 1 was used to monitor a water sample for the presence of paraoxon (an organophosphorus compound). This example utilizes an enzyme (organophosphorus hydrolase) to directly catalyze the hydrolysis of the target compound. The hydrolysis of the target compound causes the production of acidic byproducts, which result in a reduced solution pH.

Water was continuously sampled from a point source by withdrawing a constant flow (15 ml/hr) with a single pump. The water stream was delivered to a 100 mg enzyme polymer (50 mg organophosphorus hydrolase per gram polymer). The effluent color remained clear with a pH of 7.8 (the pH of tap water used) as long as the sample was free of organophosphorus compounds. Paraoxon was added to the inlet water stream (0.5 mM) and caused a reduction in pH to 5.8. While this example utilized a pH meter to monitor a signal response, the use of a pH sensitive dye as described in example 4 is also viable.

Whereas particular embodiments of the instant invention have been described for the purposes of illustration, it will be evident to those persons skilled in the art that numerous variations and details of the instant invention may be made without departing from the instant invention as defined in the appended claims.

What is claimed is:

1. An enzyme-based environmental monitoring device for detecting a target analyte comprising:
   an immobilized enzyme;
   a mechanism for continuously or coordinated intermittently delivering an environmental sample to said immobilized enzyme, wherein said environmental sample optionally contains a target analyte;
   a mechanism for continuously or semi-continuously delivering an enzyme substrate compound and optionally a pH sensitive dye to said immobilized enzyme; and
   one or more sensors located at a point downstream of the area of interaction of said immobilized enzyme, said environmental sample, and said enzyme substrate compound, for detecting for extended periods of operation the level of enzyme activity of said immobilized enzyme and presence, if any, of said target analyte, wherein said target analyte acts as an enzyme inhibitor in the presence of said immobilized enzyme and said enzyme substrate compound, and wherein said environmental sample is either water, air, or a combination thereof.

2. The device of claim 1 wherein said immobilized enzyme is trapped in an immobilization matrix.

3. The device of claim 2 wherein said immobilized enzyme is covalently bonded to a polymer matrix.

4. The device of claim 1 wherein said immobilized enzyme is a hydrolase enzyme.

5. The device of claim 3 wherein said immobilized enzyme is butyrylcholinesterase and further wherein said target analyte is a cholinesterase inhibitor.

6. The device of claim 2 one wherein said enzyme substrate compound is selected from one or more of a group comprising acetylcholine and butyrylcholine and further wherein said immobilized enzyme is selected from a group comprising is acetylcholinesterase and butyrylcholinesterase.

7. The device of claim 2 wherein said enzyme substrate compound is benzoyl-arginine-ethyl-ester and further wherein said immobilized enzyme is papain.

8. The device of claim 2 wherein said enzyme substrate compound is urea and further wherein said immobilized enzyme is urea aminohydrolase.

9. The device of claim 4 wherein said one or more sensors are selected from a group consisting of one or more pH electrodes and one or mole color readers.

10. The device of claim 1 wherein at least one of said environmental sample or said enzyme substrate compound is delivered to said immobilized enzyme intermittently or continuously.

11. The device of claim 1 wherein said environmental sample and said enzyme substrate compound are delivered to said immobilized enzyme simultaneously.

12. The device of claim 1 that is capable of alternating the flow of the delivery of said environmental sample to said immobilized enzyme, and then delivering said enzyme substrate compound to said immobilized enzyme in a repetitive pattern such that either said environmental sample is delivered to said immobilized enzyme for one time period or said enzyme substrate compound is delivered to said immobilized enzyme for another time period.

13. The device of claim 9 wherein said color reader is a RGB color to frequency converter.

14. The device of claim 9 wherein data read from said sensors are recorded for later analysis.

15. The device of claim 14 wherein said data is stored on-board said device.

16. The device of claim 14 wherein said data is directly output from said device.

17. The device of claim 14 wherein said data is wirelessly transmitted by said device.

18. The device of claim 1 wherein said mechanism for delivering said environmental sample is selected from a group comprising pumps and fans.

19. The device of claim 9 further comprising a microcontroller for collecting and analyzing said data and for determining if said target analyte is present in said environmental sample by comparing said data to a known baseline.

20. The device of claim 17 further comprising an alarm for providing notification of the presence of said target analyte in said environmental sample.

21. An enzyme-based environmental monitoring device for detecting a target analyte comprising:
    an immobilized enzyme;
    a mechanism for delivering an environmental sample to said immobilized enzyme, wherein said environmental sample optionally contains a target analyte;
    a mechanism for delivering an enzyme substrate compound and optionally a pH sensitive dye to said immobilized enzyme; and
    one or more sensors for detecting the level of enzyme activity of said immobilized enzyme and presence, if any, of said target analyte, wherein said target analyte acts as an enzyme inhibitor in the presence of said immobilized enzyme and said enzyme substrate compound, and wherein said immobilized enzyme is a hydrolase enzyme, wherein one or more of said sensors are selected from the group consisting of one or more pH electrodes and one or more color readers, wherein data read from said sensors are recorded are recoded for later analysis, and wherein said data is wirelessly transmitted by said device, and wherein a plurality of sensors are used and further wherein said alarm is activated only if all of said plurality of sensors return consistent data.

22. An enzyme-based environmental monitoring device for detecting contamination in a sample of water or air comprising:
    an immobilized enzyme covalently bonded with a polymer to form an immobilization matrix;
    a first pump or fan for continuously or coordinated intermittently delivering a stream of environmental water or air to said immobilization matrix;
    a second pump for continuously or semi-continuously delivering an enzyme substrate compound and optionally a pH sensitive dye compound to said stream of water or air prior to its delivery to said immobilization matrix; and
    one or more sensors located at a point downstream of the area of the interaction of said immobilization matrix, said environmental sample, and said enzyme substrate, for detecting the level of enzyme activity at said immobilization matrix.

23. The device of claim 20 further comprising a color reader for detecting changes in the color of said pH sensitive dye compound at said immobilization matrix.

24. The device of claim 21 further comprising a pH electrode for detecting changes in the pH of said stream of water or air after its passage through said immobilization matrix.

25. The device of claim 22 further comprising a computer for reading data output from said sensors and for analyzing said data to determine if said sample of water or air is contaminated.

* * * * *